United States Patent
Evans et al.

(10) Patent No.: US 8,911,406 B2
(45) Date of Patent: Dec. 16, 2014

(54) GUIDE WIRE EXCHANGE CATHETER SYSTEM

(75) Inventors: Douglas G. Evans, Downingtown, PA (US); John E. Nash, Chester Springs, PA (US); Steven J. Link, Phoenixville, PA (US)

(73) Assignee: Kensey Nash Corporation, Exton, PA (US)

( * ) Notice: Subject to any disclaimer, the term of this patent is extended or adjusted under 35 U.S.C. 154(b) by 2326 days.

(21) Appl. No.: 11/457,147

(22) Filed: Jul. 12, 2006

(65) Prior Publication Data

US 2008/0082049 A1    Apr. 3, 2008

(51) Int. Cl.
*A61M 5/178* (2006.01)
*A61M 25/09* (2006.01)
*A61M 25/01* (2006.01)

(52) U.S. Cl.
CPC ... *A61M 25/09041* (2013.01); *A61M 2025/018* (2013.01); *A61M 25/0172* (2013.01); *A61M 2025/0183* (2013.01)
USPC .................................................. 604/165.02

(58) Field of Classification Search
CPC ..................... A61M 25/09; A61M 2025/0183; A61M 2025/09125; A61M 25/09041; A61M 25/0169; A61M 2025/09116
USPC ............... 604/103.04, 164.13, 164.1, 164.07, 604/164.01, 164.09, 164.08, 165.01, 604/165.02, 165.03, 164.12, 523–532, 604/95.01–95.05; 606/1, 200, 434, 439; 600/585
See application file for complete search history.

(56) References Cited

U.S. PATENT DOCUMENTS

| | | | |
|---|---|---|---|
| 4,932,413 A | 6/1990 | Shockey et al. | |
| 4,947,864 A | 8/1990 | Shockey et al. | |
| 5,192,268 A * | 3/1993 | Shiber | 604/540 |
| 5,261,879 A * | 11/1993 | Brill | 604/96.01 |
| 5,318,527 A | 6/1994 | Hyde et al. | |
| 5,976,093 A | 11/1999 | Jang | |
| 6,071,285 A * | 6/2000 | Lashinski et al. | 623/1.11 |
| 6,142,987 A | 11/2000 | Tsugita | |
| 6,482,211 B1 * | 11/2002 | Choi | 606/108 |
| 6,537,294 B1 | 3/2003 | Boyle et al. | |
| 6,605,062 B1 | 8/2003 | Hurley et al. | |

(Continued)

FOREIGN PATENT DOCUMENTS

| | | |
|---|---|---|
| WO | WO-00/62851 A1 | 10/2000 |
| WO | WO-01/43809 | 6/2001 |
| WO | WO-2005/011788 | 2/2005 |
| WO | WO-2005/112798 | 12/2005 |

*Primary Examiner* — Aarti B Berdichevsky
*Assistant Examiner* — Bradley Osinski
(74) *Attorney, Agent, or Firm* — Jeffrey R. Ramberg (57) ABSTRACT

A guide wire exchange system including an elongate, flexible, guide wire exchange catheter capable exchanging one guide wire for another in a safe, efficient, and secured manner, where a primary guide wire, after having been advanced through the body, is to be replaced with a secondary guide wire that is to be securely advanced through the body to the target site by the advancement of the exchange catheter over the path of the primary wire. The exchange catheter may include a securement element in order to releasably secure at least one guide wire to the exchange catheter at or near the distal end of the exchange catheter. Once secured, both the exchange catheter and the secured guide wire(s) may be advanced or retracted in a synchronous manner, without the possibility of divergence at the distal ends of the secured components as they are being manipulated by an operator.

39 Claims, 6 Drawing Sheets

(56) References Cited

U.S. PATENT DOCUMENTS

| | | |
|---|---|---|
| 6,652,505 B1 | 11/2003 | Tsugita |
| 6,746,466 B2 * | 6/2004 | Eidenschink et al. ........ 606/194 |
| 7,438,720 B2 * | 10/2008 | Shaked ........................ 623/1.11 |
| 7,753,951 B2 * | 7/2010 | Shaked et al. ................ 623/1.35 |
| 2001/0001117 A1 | 5/2001 | Chow |
| 2002/0095141 A1 | 7/2002 | Belef et al. |
| 2003/0153934 A1 | 8/2003 | Gerberding |
| 2004/0059372 A1 | 3/2004 | Tsugita |
| 2005/0027249 A1 * | 2/2005 | Reifart et al. ............ 604/103.04 |
| 2005/0209673 A1 * | 9/2005 | Shaked ........................ 623/1.11 |
| 2006/0106448 A1 * | 5/2006 | Shaked ........................ 623/1.11 |

* cited by examiner

GUIDE WIRE EXCHANGE CATHETER SYSTEM

BACKGROUND OF THE INVENTION

The present invention relates to guide wires, catheters and elongate devices used in the vessels, ducts, and lumens of a living being, and more particularly to a system for facilitating the delivery and exchange of such catheters, devices, and guide wires to various locations within the body of a living being.

As will be appreciated by those skilled in the art, various medical procedures involve the use of catheters and guide wires that are inserted into various locations within a living being. By way of example, for the treatment of some vascular diseases, such as atherosclerosis, it is common practice to insert an instrument (e.g., catheter, guide wire, etc.) into a vessel to perform a procedure that reduces or eliminates a restriction or stenosis. Such procedures, known as percutaneous catheterization intervention (PCI), typically involve several steps. To begin, an initial puncture is created in a vessel that is typically remote from the stenosis. Next, a guide wire is inserted through the puncture and threaded into the vessel. A guiding catheter is then advanced into the patient's arteries. A guide wire is then advanced through the guiding catheter and, for the treatment of coronary disease, into the patient's coronary arteries. The guide wire is maneuvered by advancing and rotating the distal tip, which normally has an asymmetric "J" shape imposed on it to enable the selection of various branches of the coronary vasculature. Once the wire is in the desired position, a diagnostic or therapeutic catheter, which has a lumen or other means adapted to receive the guide wire, is then guided along the wire to the desired location.

In the course of a typical PCI, for example, an angioplasty procedure, the catheter has a distally mounted balloon that can be placed, in a deflated condition, within the stenosis, and then inflated to dilate the narrowed lumen of the blood vessel. Such balloon dilation therapy is generally referred to as percutaneous transluminal angioplasty (PTA). Percutaneous transluminal coronary angioplasty (PTCA) is used when the treatment is more specifically employed in vessels of the heart. PTCA is used to open coronary arteries that have been occluded by a build-up of cholesterol fats or atherosclerotic plaque. The balloon at the distal end of the catheter is inflated, causing the site of the stenosis to widen. In some cases, a stent, a cylindrically shaped device formed from wire(s) or a metal tube, is placed at the site of the restriction to act as a prosthesis that provides support to the body lumen. In addition to angioplasty and stealing procedures, other diagnostic and therapeutic procedures require the use of wires and catheters, such as drug delivery, embolic protection, angiography, atherectomy, imaging and other treatments known in the art.

During these procedures, the guide wire plays an important role in guiding the diagnostic or therapeutic device (e.g., catheter) to the desired location in the patient's body. For example, one difficulty that can be encountered in the procedure is the inability to cross the lesion or stenosis with the distal end of the guide wire. This can be the result of a variety of situations, including a tight stenotic lesion with insufficient lumen patency to allow passage of a guide wire. In other instances, the vessel can be completely blocked as in the case of a chronic total occlusion (CTO). In cases such as these, the physician may need to utilize a different guide wire and thus replace an in-situ wire with another having different construction, structure or properties, e.g., floppy-tip design or shape, stiffness, etc. The need to withdraw an already placed guide wire also occurs when the distal tip of the guide wire needs to be reshaped to pass a blockage or navigate into the desired vessel. Because of this, there exists a need for the physician to be able to exchange guide wires while supporting a pre-positioned guide wire to facilitate crossing of a difficult lesion.

The manner in which the catheter integrates with the guide wire during the procedure can have significant impact on she timing, ease of use, and ultimate success of the procedure. In general, there are four types of wire-catheter systems:
1. Over-the-wire (OTW),
2. Multi-Exchange (MX),
3. Rapid Exchange (RE), and
4. Fixed Wire (FW).

OTW, MX and RE catheters require the use of a guide wire that is separate from the catheter while a FW catheter has an integral guide wire. An OTW catheter comprises a guide wire lumen that extends the entire length of the catheter. The guide wire is disposed entirely within the catheter guide wire lumen except for distal and proximal portions of the guide wire, which extend beyond the distal and proximal ends of the catheter respectively. An MX catheter is arranged such that it has an over-the-wire configuration while the catheter is within the patient's body, but the wire exits the side of the catheter through a zipper-like, longitudinal slit configuration at a location outside the body.

OTW and MX catheters provide a full length guide wire lumen, whereas RE catheters provide a short guide wire lumen only at or near the distal end. However, traditional OTW, MX and traditional RE catheters do suffer some shortcomings. For example, it often becomes necessary, in the performance of a PCI, to exchange one indwelling catheter for another catheter. In order to maintain a guide wire in position while withdrawing an OTW catheter, the guide wire must be gripped at its proximal end to prevent it from being pulled out of the blood vessel with the catheter. For example, a PTCA catheter, which may typically be on the order of 135 centimeters long, is longer than the proximal portion of the standard guide wire that protrudes out of patient. Therefore, exchanging an over-the-wire PTCA catheter requires an exchange guide wire of about 300 centimeters long, whereas a standard guide wire is about 165 centimeters long. Wires of this length can be difficult to control in the surgical field, and it is not uncommon for a portion of such a long wire to inadvertently touch the floor or other non-sterile location in the catheterization laboratory, thereby requiring removal of the wire from the patient and the reinitiating of the procedure with a new wire. Other techniques are known in the art for performing wire exchange with OTW catheter yet regardless of which exchange process is used, the very long exchange guide wire is awkward to handle, often requiring at least two operators to perform the procedure.

RE catheters were developed in an attempt to simplify the procedure for exchanging wires and catheters. Catheters of this type are formed so that the guide wire is located outside of the catheter except for a short guide wire lumen that extends within only a comparatively short distal segment of the catheter. The RE catheter's proximal exit port for the guide wire is typically located about 5 cm (2.0 in) to 30 cm (11.8 in) proximal to the catheter's distal end. In use, the guide wire is placed initially in the patient's vascular system. The distal segment of the RE catheter then is threaded onto the wire. The catheter can be advanced alongside the guide wire with its distal segment sliding along the guide wire. The RE catheter can be removed and exchanged for another RE catheter without the use of a very long exchange guide wire and without requiring withdrawal of the initially placed guide wire.

However, one shortcoming associated with RE catheters is that it is not possible to exchange guide wires in an indwelling RE catheter, as can be done with OTW catheters. A guide wire can be withdrawn, sometimes accidentally, from the proximal guide wire port, thus derailing an indwelling RE catheter. However, neither the first guide wire, nor a replacement guide wire, can be directed back into the catheter's proximal guide wire port, which is located within the patient.

In addition to exchanging catheters over guide wires, it is also sometimes desirable to exchange one guide wire for another guide wire having a different feature. Over the years, specialty guide wires have been developed possessing different characteristics with respect to size, length, flexibility, tip shape, etc. to provide the physician with the proper wire for each unique medical circumstance. For example, when a physician encounters highly tortuous anatomy, a relatively soft and flexible guide wire is typically employed because they can be easily placed at the desired location and they have enough stiffness for guiding a flexible diagnostic angiography catheter through the vasculature. However, a shortcoming of these highly flexible wires is that their degree of flexibility makes them poor wires for guiding stiffer and larger therapeutic catheters (e.g., stent delivery catheters) through the same tortuous vasculature region. These stiffer catheters often require a guide wire that is relatively stiffer as well. In these instances it is desirable to place a second, more suitable, guide wire at the desired treatment site.

It is known in the art that dual lumen catheters can be used to exchange one wire for another. The first lumen of the catheter is used to guide the catheter along the initial wire and the second lumen is then used to deliver a second wire to the location of the first. A shortcoming of these systems is that the presence of dual lumens extending the length of the catheter makes them quite large (i.e., in effective diameter), limiting how far they may be advanced into the body, as well as affecting their flexibility. Furthermore, they require the use of double length wires, which is a tedious procedure with accompanying safety issues, as described previously.

Alternatively, it is known in the art to employ a rapid exchange delivery sheath, which utilizes only a short lumen segment for guiding an exchange catheter over the primary guide wire. This allows the primary wire to be of a shorter length, however the second wire must be double length to allow removal of the exchange catheter.

MX catheters include a longitudinal slit extending most of the length of the catheter, through which a wire may be removed laterally, or "peeled off". At the distal end of the catheter is a short segment lacking the longitudinal slit, similar in nature to the short, segment of a RE catheter. In use, a guide wire may be inserted at the proximal end of the catheter, and advanced through the central lumen of the catheter, much like an OTW catheter. However to remove the MX catheter, and not remove the wire, the proximal end of the wire (outside of the body) is laterally removed through the slit provided in the catheter wall. While holding the wire in position, the catheter is retracted, and removed from the wire through the length of the longitudinal slit of the catheter, in effect, peeling the catheter away from the wire as the catheter is retracted. As the catheter is peeled off, and the catheter is retracted until the wire encounters the distal end of the slit, whereupon there remains a short segment of the catheter that may be removed in a manner similar to that for a RE catheter. The MX procedure offers the benefit of an internal lumen delivery of the wire, similar to an OTW, but allows the user to avoid a double length catheter, similar to a RE catheter. However, the required "peeling-off" procedure is tedious as it requires holding onto the proximal end of the wire, and careful removal is required, as great care must be taken to ensure that the peeling off procedure does not crimp or otherwise damage a wire, and also to ensure that there are no movements as the wire is pulled through the longitudinal slit that would dislodge the distal end of the wire from the target location or vessel. The "peeling off" procedure may be acceptable with robust, large diameter wires, however the procedure is ill suited for use with specialized, narrow diameter guidewires, as may be required to reach far into tortuous vasculature or effect a difficult crossing of a lesion, as these wires are more sensitive to damage, such as crimping or breaking, when the MX catheter is retracted and removed.

It is known in the art, for example, in U.S. Pat. Nos. 6,537,294 and 6,652,505, 6,142,987, and published US Application Nos. 2002/0095141 and 2004/0059372, that a catheter can be constructed where two short lumen segments are mounted on a mandrel or third wire. This device is used to deliver a filter device, housed in one short lumen, along a guide wire, housed in the second short lumen. A short-coming of this system is that there is no method for securing she filter in the short monorail segment other than the surface contact between the expandable filter and the internal surface of the short lumen of the monorail.

U.S. Pat. No. 4,947,864 describes a guide wire exchange catheter employing a MX procedure for peeling away the exchange catheter after the satisfactory placement of a second (replacement) guide wire. As the operator advances the exchange catheter into the patient, he also grasps a second (replacement) guide wire which has its distal end directed through the distal end portion of the exchange catheter. While grasping both the exchange catheter and the second guide wire at a location outside of the patient, the operator simultaneously advances both the exchange catheter and the replacement guide wire further into the patient, following along the first guide wire. The '864 patent does not provide for a way to secure the distal end of the second guide wire in place within the exchange catheter, therefore the operator must take great care to simultaneously grasp and advance the wire and catheter together. Once at the desired site, the wire may be left in place and the catheter must then be peeled off, taking care not to crimp the wire, nor dislodge it from the desired site.

U.S. Pat. No. 6,605,062 (Hurley et al.) describes a catheter for guide wire support or exchange having a longitudinal slit in the catheter to allow a guide wire exchange using a MX procedure where the catheter is peeled off of a second guide wire while the catheter is being retracted. Hurley et al. also provide for an axial support member secured to the elongate shaft to provide axial rigidity to the catheter. There is no provision for releasably locking or securing a guide wire in place within the exchange catheter.

What is needed is a reliable easy to use system to exchange one guide wire for another with out the need for double length guide wires. There is further a need where the delivery of the secondary guide wire, which is to be exchanged with the initial guide wire, is accomplished in a rapid, safe, and secure manner, where there is provided an exchange or shuttle catheter which is advanced over a primary wire, and where the exchange catheter securely carries or pulls along a second wire to the target site. Furthermore, there is a benefit to providing an elongate, flexible device that has a low, compact profile at the distal end to better navigate tortuous anatomy. Moreover, the system should be relatively easy to insert and remove from the patient's vasculature.

SUMMARY OF THE INVENTION

The present invention provides a delivery system, which can be utilized to place at least one additional guide wire in the vicinity of a first guide wire without the need for double length wires; large bulky dual multi-lumen exchange catheters; or tedious, peeling-off procedures that may damage the guide wire.

Additionally, having a guide-wire remain in-place, while another may be advanced, such that the distal end of the second guide-wire may be easily and rapidly advanced to the location of distal tip of the first (in-place) wire, will save procedure time and reduce complications. It takes several minutes to advance the first guide-wire to a coronary site, and perhaps substantially longer for tortuous areas in the anatomy or for difficult lesions. Using the first guide-wire to "guide" the second, by way of the embodiments of the present invention, will allow the tracking of the second guide-wire along the first guide-wire such that it may easily be placed in the same site in a period of time that maximizes patient safety, for example, having placement times for the second guide wire under one minute.

One embodiment of the present invention provides for a shuttle or exchange catheter having two separate lumen segments formed at or near the end of the catheter, one segment for receiving the primary guide wire and another segment for receiving the secondary guide wire. The primary guide wire is maneuvered by the physician through the tortuous anatomy of the patient into the area of treatment, using techniques known in the art. The second guide wire can then be loaded into an embodiment of the present invention serving as the exchange or shuttle catheter, which can then be guided along the primary wire to the desired location. Thereafter, the first guide wire can be retracted into the lumen at the distal end of the shuttle catheter in preparation for the advancement of the second wire. If desired, the first wire can be completely removed from the patient. The second wire can then be advanced through the second lumen of the shuttle catheter until it is directed into the desired location within the vessel. The shuttle catheter can then be removed from the patient. Other elongate devices (e.g., infusion, therapeutic, diagnostic, etc.) can then be easily and rapidly guided to the desired location over the second guide wire.

These and other advantages of the invention will become more apparent from the following detailed description of the various embodiments of the invention when taken in conjunction with the accompanying exemplary drawings.

DETAILED DESCRIPTION OF PREFERRED EMBODIMENTS

The present invention is an improved guide wire exchange system including an elongate, flexible, guide wire exchange catheter capable of being directed through vasculature of a body, as well as a method of rapidly, and safely, exchanging guide wires in a body. The system addresses the need to be able to exchange one guide wire for another in a safe, efficient, and secured manner, where a primary guide wire, after having been advanced through the body, is to be replaced with a secondary guide wire that is to be securely advanced through the body to the target site by the advancement of the exchange catheter along the path of the primary wire. The replacement or secondary wire preferably provides a quality lacking in the primary guide wire. For example, a primary guide wire may be relatively stiff, in order to be advanced to a desired location, thereupon to be replaced with a relatively less stiff guide wire that would allow the traversal of more tortuous vasculature. Alternatively, the second guide wire may be more robust, or provide increased pushability or stiffness, in order to be advanced across a difficult lesion. Furthermore, a replacement guide wire may be shaped differently at its distal end than a primary guide wire, in order to more effectively steer the wire into a desired vessel, or be tailored specifically for a purpose for which the primary guide wire is less suited, for example, where the replacement guide wire is an electrophysiology wire. It is recognized that the guide wires may differ in several characteristics, including, for example, the manner of construction, design, materials, alloys, shape memory, diameter, distal end shape or design, ability to be customized and shaped, flexibility, stiffness, etc.

Figure 1:
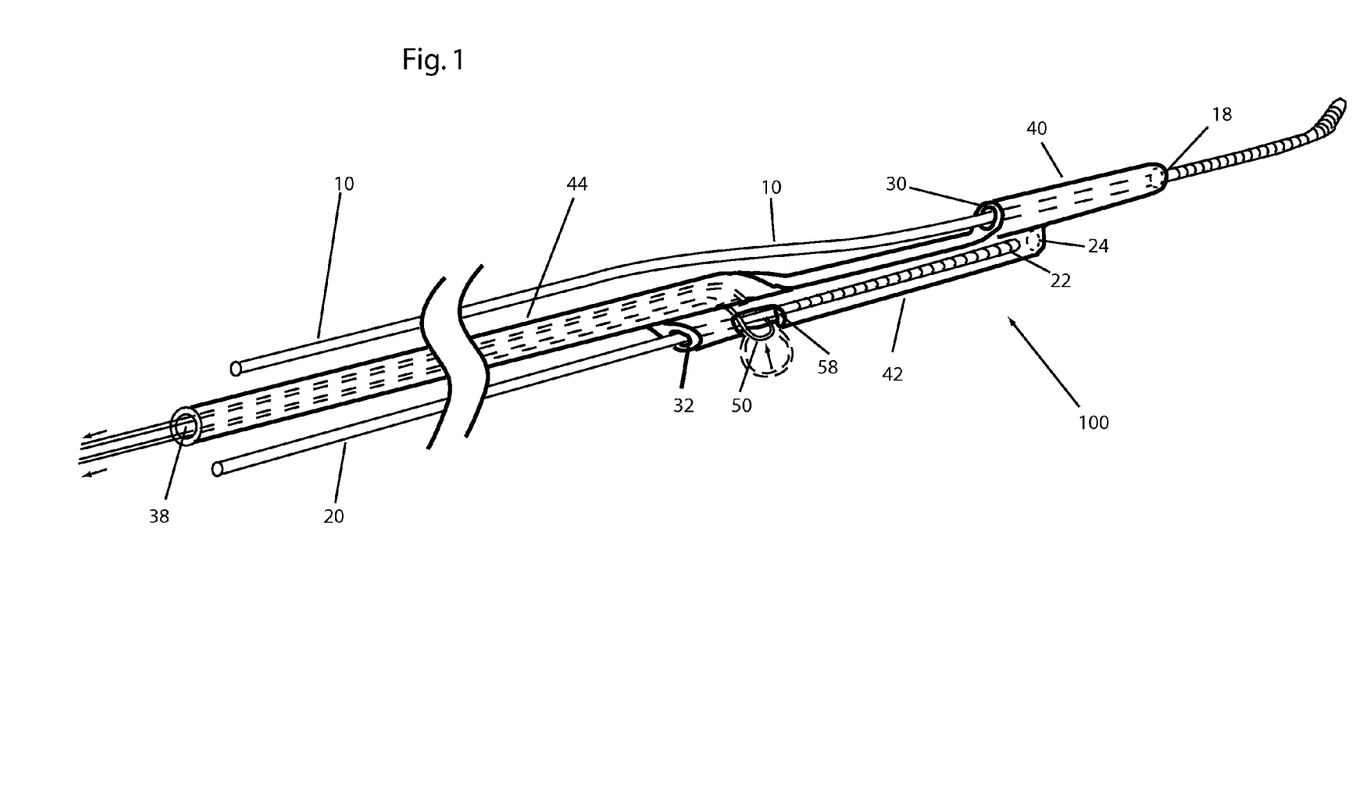
FIG. 1 is an illustration of one embodiment of the guide wire exchange system of the present invention.

The embodiment of the guide wire exchange system depicted in FIG. 1 includes at least two guide wires, and an exchange or shuttle catheter having a means to secure at least one wire securely in place. The exchange catheter provides for the exchange of guide wires and incorporates at least one reversible securement mechanism in order to releasably secure at least one guide wire to the exchange catheter at or near the distal end of the exchange catheter. Once secured, both the exchange catheter and the secured guide wire(s) may be advanced or retracted in a synchronous manner, without the possibility of divergence at the distal ends of the secured components as they are being manipulated by an operator. Additionally, she exchange catheter may be repeatedly secured and released, allowing for multiple placements, or movements.

The exchange catheter of the present invention may be manufactured using techniques and materials known in the art for the manufacture of catheters and guide wires, including those techniques and materials of rapid exchange catheters. Additionally, it is recognized that the exchange catheter of the present invention may have similar lengths, and dimensions as known for the manufacture of prior art catheters and guide wires.

In this embodiment, the distal most end of the exchange catheter 100, along with the relative arrangement of a first or primary wire 10 and a second or secondary wire 20, is shown. The catheter 100 may be considered to have at least three distinct segments, including a first segment 40, a second segment 42, and a main body segment 44. The first and second segments, 40 and 42 respectively, are located near the distal end of exchange catheter 100. Each of these first and second segments provides a short lumen or monorail through which a primary wire 10 or a secondary wire 20 may be directed, as may be used with rapid exchange catheters. It is recognized that additional segments may be provided for use with additional wires.

The first segment 40 is the most distal segment of the exchange catheter 100, and creates a tubular lumen having a distal opening 18, and a first segment proximal opening 30. The second segment 42 also creates a tubular lumen having a second segment distal opening 24 and a second segment proximal opening 32. Optionally, a lateral opening 58 is provided in the wall of the second segment to allow for the operation or placement of a securement element 50 (to be discussed later). The first segment 40 is axially separated from the main body segment 44, though, as depicted, it may be oriented along the main axis of the main body segment. The second segment 42 is oriented substantially parallel to both the first segment 40 and main body segment 44, but in a position that is off-axis, or laterally adjacent to the main axis of the main body segment 44.

Figure 3:
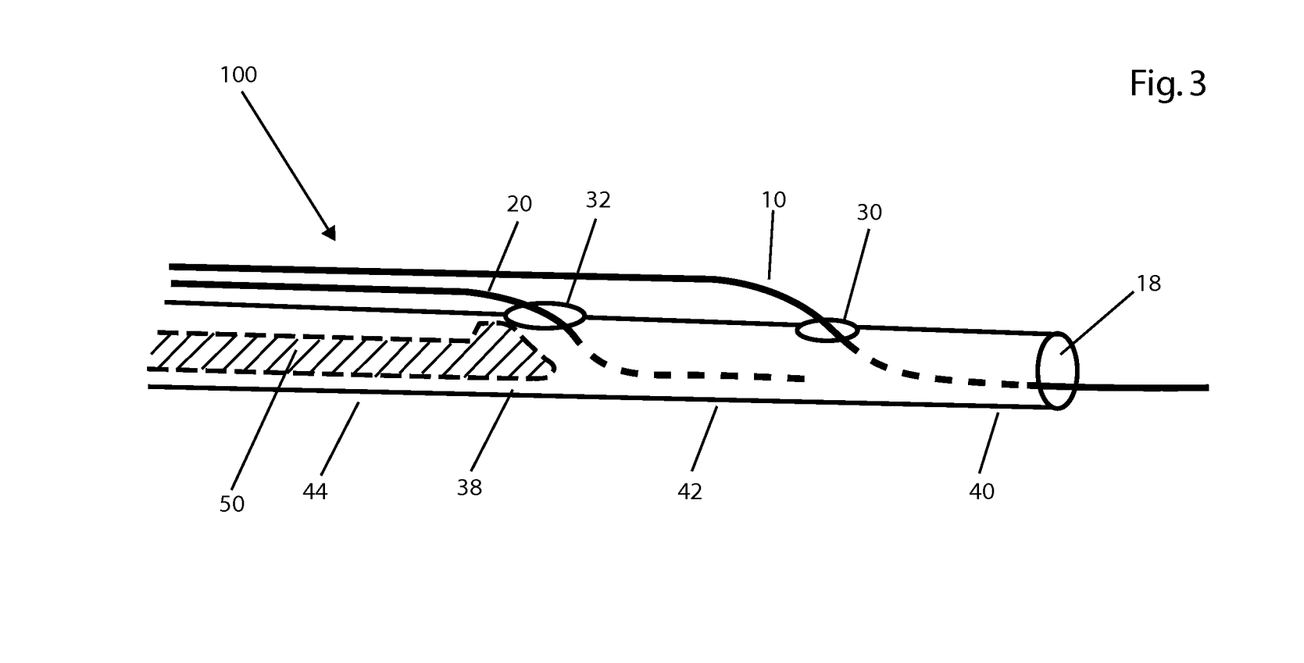
FIG. 3 is an illustration of yet another embodiment of the guide wire exchange system of the present invention, depicting the distal end of the exchange catheter having a tubular construction.

In an alternative embodiment, as seen in FIG. 3, the first and second segments, 40 and 42 respectively, together with the main body segment 44, form a continuous tubular form as the two distal segments are in alignment with the main axis of the main body segment 44. In this embodiment, the first segment 40 is at the distal most portion of the exchange catheter 100, having a distal opening 18 and a proximal opening 30 arranged laterally in the wall of the catheter. The second segment 42 is proximally adjacent to the first segment, and distally adjacent to the main body segment 44, and the second segment has a proximal opening 32. As the first and second segment share a tubular structure, there is no distinct opening identifying the distal end of the second segment 42, rather the tubular construction simply continues into the first segment 40. Each of the first and second segments 40 and 42 respectively, has proximal openings that are formed laterally in the wall of the tubular construction. The distal opening 18 of the first segment would also serve as an exit for the wire directed through the second segment, as any wire advanced distally through the second segment's interior lumen would also be advanced through the first segment to exit at the distal opening 18. The respective proximal openings 30 and 32 for the first and second segments 40 and 42 may or may not be in oriented in radial alignment with each other, and may preferably be out of alignment with each other, and may, for example, be beneficial in preventing the first and second guide wires from becoming entangled. There may be a benefit to providing a loading element that would assist in deflecting the proximal end of the primary wire 10 out the proximal opening 30 of the first segment 40 as wire 10 is being backloaded into the exchange catheter 100. Such a loading element may be a curved tool arranged to be inserted laterally into opening 30 to catch and deflect the proximal end of wire 10 as it is backloaded, and removed after the wire 10 is directed out the opening 30. Alternatively, the loading element may be in the form of a one-way door or flap arranged inside the exchange catheter 100 at a location adjacent to and proximal to the opening 30, which would cause the deflection of the proximal wire 10 as it is backloaded in a proximal direction, causing the wire to exit out opening 30, however the loading element would be capable of deflecting in order to allow the later advancement of second wire 20 in a distal direction beyond the flap and through the end of the exchange catheter.

Referring again to FIG. 1, in an embodiment where the first and second segments are arranged parallel to each other, but not sharing the same axis, the first and second segments may be provided in an arrangement where they have at least some longitudinal overlap along the length of the catheter. Specifically, FIG. 1 depicts the proximal portion of the first segment 40 and the distal portion of the second segment 42 having at least some longitudinal overlap. Alternatively, the first and second segment may be longitudinally distinct, having no overlap between their respective lengths along the exchange catheter, simply by adjusting the respective lengths of the segments of the device, such that each segment is at a distinct longitudinal location relative to the other segments. Similarly, there may or may not be longitudinal overlap between the proximal portion of the second segment and the distal portion of the main body segment; note that FIG. 1 depicts at least some longitudinal overlap between the main body segment 44 and the second segment 42.

The main body segment 44 may be a long tubular section forming the majority of the length of the exchange catheter 100, and while in use, at least the proximal end is arranged to remain outside of the body, such that the operator may grasp and manipulate the proximal end of the exchange catheter 100. The proximal end of the exchange catheter may optionally feature a handle or other feature that facilitates manipulation of the exchange catheter, and may be in the form of, or in addition to, an actuation device for the securement mechanism, to be discussed later. Preferably, the main body section has physical characteristics similar to those found for adequate performance of catheters, though, it is also recognized that the main body section may be of smaller dimensions than typical catheters. For example, the dimensions and physical characteristics of the main body section are preferably able to provide good torqueability and pushability that enable the exchange catheter 100 to be effectively advanced into the patient.

Additionally, the main body segment 44 may be constructed using various techniques, including those known in the art for the construction of catheters and medical devices, such as incorporating regions that vary by construction or material. For example, regions may provide variable or constant diameters and wall thicknesses. Furthermore, regions may be manufactured from different materials (e.g., polymer, alloys, etc.) such as may be used to provide enhanced performance for the device in qualities including flexibility, stiffness, or shape memory, tactile sensation, among others. The guide wire exchange catheter 100 may be provided with additional features that improve the performance or use of the catheter, including, for example, radiopaque markers, coatings may be applied to reduce friction or increase wettability, zones of enhanced flexibility or increased stiffness may be provided, additional stiffening elements may be employed, etc. For the construction of the main body segment featuring, in one embodiment, a varied wall thickness as may be utilized for providing zones of varying flexibility and pushability, the main body segment may further be subdivided into small sub-sections, each providing differing wall thicknesses or other physical characteristics. For example, the main body segment may feature a reduction in outside diameter over its length, as may be created by having either a stepped down or tapered design, preferably having a wider outside diameter and larger wall thickness at a proximal portion, and a narrower outside diameter and thinner wall thickness at the distal end of the main body segment. It is recognized that the main body segment may be manufactured from a single tube having varied wall thicknesses and outside diameters, though it is also recognized that the main body segment may have a main hypotube comprising substantially the entire length of the main body segment, and further featuring, placed at or near the proximal end of the main hypotube, additional lengths of hypotube arranged concentrically around the main body hypotube in order to provide a stepped down outside diameter from proximal to distal end of the main body segment.

Also depicted in FIG. 1 is one possible embodiment of the securement element 50, provided to releasably secure the exchange catheter 100 and a second guide wire 20 to each other, such that they are not capable of being advanced or retracted independently of each other. The securement element may be in the form of a filament that has been doubled over to create at its distal end a loop around the second guide wire 20, and the filament ends are extended proximally back through a lumen provided by the interior dimensions of main body segment 44. The filament ends of securement element 50 extend to the proximal end portion of the exchange catheter 100, where the ends can be manipulated by the operator. In use, the operator may selectively apply tension to the ends of the filament of the securement element 50, thereby constricting the loop such that it tightens around the second guide wire 20. Continued tension on the filament ends of the securement element 50 will grip and secure the second guide wire 20 in a fixed location within second segment 42 of the exchange catheter 100. The securement element 50 may be used to secure the second guide wire 20 distal portion 22 shown here within the interior of the second segment 42. Upon release of the applied tension at the distal end of the securement element 50, the loop is relaxed, and loosens the grip on second guide wire 20, such that the second guide wire may be slidably manipulated through, second segment 42, independent of any movement of the exchange catheter 100. It is recognized that a loop opening 58 may be provided in the lumen wall of the second segment, through which the filament or loop of the securement element 50 may be extended. Such an optional loop opening 58 may be useful or provided for ease of manufacturing the complete system, or alternatively to accommodate the loading and unloading of the second wire into the loop of the filament, or even to allow a visual confirmation that the loop is properly placed around the second guide wire 20.

Figure 2A:
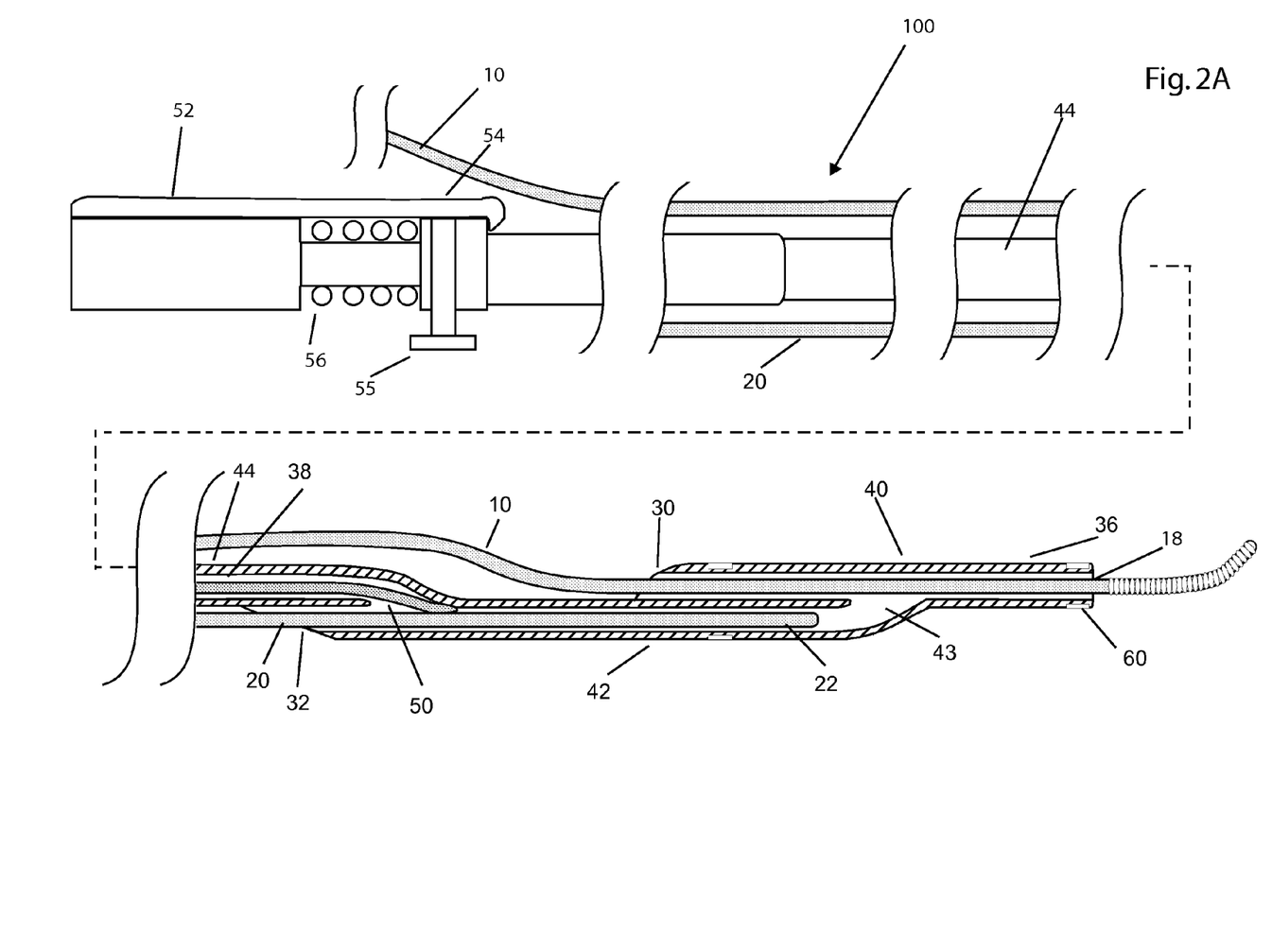
FIGS. 2A and 2B are illustrations of another embodiment of the guide wire exchange system, with only the distal region being shown as a transverse sectional illustration, where 2A depicts the second wire being maintained in a secured position relative to the exchange catheter, and 2B depicts the second wire with the securement element disengaged, such that the second wire and exchange catheter are slidably moveable independent from each other.
Figure 2B:
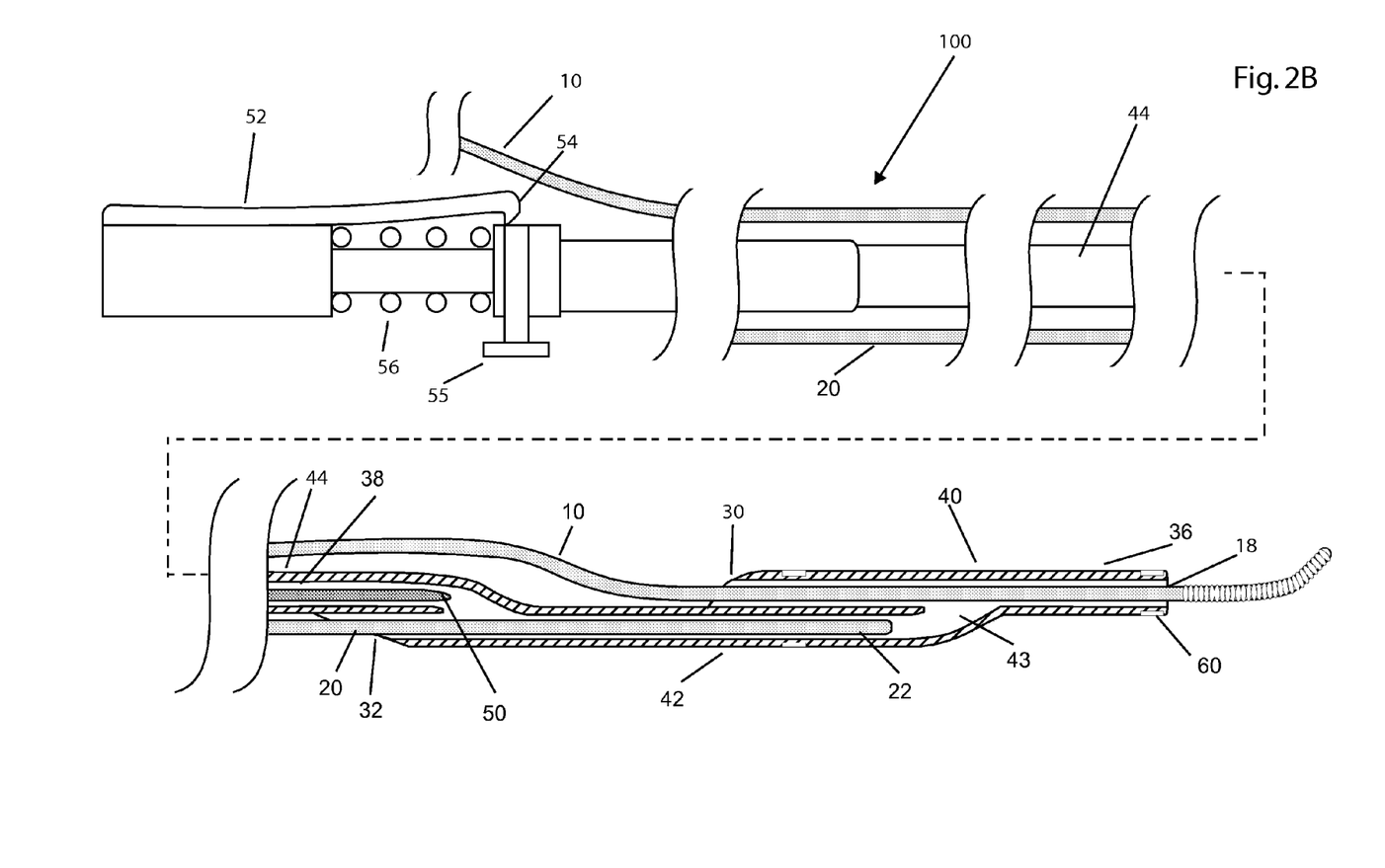

In another embodiment of the guide wire exchange system, as shown in cross-section in FIGS. 2A and 2B, there is provided another embodiment of a securement mechanism, made of at least securement element 50 and an actuator 52 for actuating the securement element. Additionally, there is depicted an alternative arrangement of the first and second segments, 40 and 42 respectively, at the distal end of the exchange catheter 100, where the second segment 42 merges with the first segment at a merger point 43, created where the distal opening of the second segment 42 communicates with the interior lumen of the first segment 40. This arrangement of she guide wire lumen segments 40 and 42, would provide for a low profile distal section that extends distally from the merger point 43, and is preferably able to slidably accommodate a single wire directed therethrough. This extended distal section 36 may allow for the exchange catheter to reach further into smaller vessels by presenting a smaller profile for the distance extending beyond the merger point 43 and extending to the distal end of the exchange catheter 100. The smaller profile may beneficially be utilized where, after advancement of the primary guide wire, the exchange catheter is advanced along the primary wire, which is directed through the first segment of the exchange catheter. Upon the exchange catheter arriving at a desired location, the operator then removes or withdraws the first guide wire, either completely, or merely from at least the extended distal portion 36 and the merger point 43. The second guide wire 20 may then released from securement and advanced distally out from the second segment 42, through the merger point 43 region, and subsequently the second wire 20 may then be advanced through the extended distal section 36, to exit out the distal opening 18 at the end of the exchange catheter 100. There may be a benefit to providing art extended distal section 36, beyond the merger point 43 with the second lumen, that is extended to some distance beyond the length typical of the short lumens found on rapid exchange catheters, where the extended region serves to provide a guide for the second guide wire to follow as it is advanced over the path previously established by the first guide wire 10, where the first wire is preferably removed or at least partially withdrawn before the advancement of the second guide wire 20. In use, the advancement and placement of various embodiments may be tracked using techniques known in the art, for example, in FIG. 2A there is provided a radio-opaque marker 60 near the distal opening 18 of the exchange catheter.

The securement element 50 provided in FIGS. 2A, 2B, and 3, preferably is arranged to secure the second guide wire while under compression, and may be in the form of a filament or rod, such as a wire, preferably being stiffer than a typical guide wire, that will effectively transmit a force applied at its proximal end to its distal end without substantial buckling or bending, however, not so rigid as to interfere with required flexibility necessary for the exchange catheter to be used within the body. It is recognized that the interior lumen 38 of the main body segment 44 may be sized to accommodate the outside diameter of the securement element with little or minimal clearance, in order to minimize any tendency of the securement element 50 to buckle or bend as force is applied, thereby allowing a more flexible design, though still capable of transmitting a securing force along the length of the securement element 50. Alternatively, the interior lumen 38 may be larger than, or provide for clearance, over the outside diameter of the securement element 50, in order to minimize friction between the securement element and the main body segment 44 as the securement element is advanced. Additionally, the increased clearance of the interior lumen 38 of the main body segment 44 provided around the securement element 50, may allow the main body segment to deliver additional materials (e.g., saline, contrast fluid, blood, therapeutic agents, biologically active agents, drugs, carbon dioxide, gas, air, solids, particulates, microspheres, etc.). The securement element may have a distal tip portion that is capable of serving to secure the second guide wire in place. For example, the securement element of FIG. 3 may in the form of a wire or rod that is smaller in diameter than the inner diameter of the main body segment, thereby providing at least some clearance between the securement element and the inner wall, and further, where the distal tip section of the securement element differs in at least one dimension, such as having an increase in size, in order to more effectively secure the second guide wire.

The deployment and withdrawal of the securement element 50 depicted in FIGS. 2A and 2B, respectively, may be performed by actuator 52 acting under the direction of the operator in order to reversibly deploy the securement element 50. Upon deployment, the securement element transmits a force applied at the proximal end down the length of the securement element, and acts upon the second wire 20. In the embodiment where the force is in the form of compression, the compressive force is conveyed down the securement element length and the distal end of the securement element pushes against the second wire to lock it in place against the second segment 42, thereby fixing or securing the second guide wire 20 in position with the guide wire exchange catheter 100. Alternatively, with reference to she embodiment shown in FIG. 1, for a securement element 50 that is arranged to engage while placed in tension, a wire or filament may have a loop arranged around the second wire, that as the force is applied, the loop is pulled taught against the second wire, pulling the second wire laterally against the second segment to lock the second wire in place.

As discussed above, the securement element 50 may be sized, shaped, formed, textured, or otherwise altered at its distal end to better fix or immobilize the second guide wire in position relative to the exchange catheter. For example, a wedge shape formed into the distal end of the securement element 50 may be effective in increasing the holding force available to prevent the shifting of the second wire 20 when the securement mechanism is actuated. Alternatively, various surface features (e.g., ridges, textured surface, coatings, etc.) or varied materials (e.g., pliable tip elements) may further be provided on the securement element 50 in order to increase the holding force upon deployment. Furthermore, the exchange catheter may be shaped or provide additional features to achieve a more secure immobilization of the second wire. For example, there may be a benefit to shaping the proximal opening of the second lumen, or providing a gripping insert (e.g., conformable o-ring) that would more securely hold the second wire, and or possibly prevent deformation, damage or crimping of either the second wire or exchange catheter as the securement element is actuated. Such an insert could be manufactured from a polymer material (e.g., pebax, etc.) that will be elastically deformable, or alternatively may be a rigid material.

As depicted in FIGS. 2A and 2B, one possible embodiment of a mechanical actuator 52 is depicted in a deployed and retracted state, respectively. In this embodiment, the actuator includes at least a resilient material 56 (e.g., a spring, elastomeric foam, etc.) that is arranged to be elastic and capable of returning substantially to its original shape after being released. For example, in the embodiment of FIG. 2A, the resilient material 56 is in the form of a spring that is compressed and maintained under compression while the actuator 52 is in a actuated position, and a holding mechanism 54 (e.g., a latch, hook, etc.) that is arranged to maintain the actuator in the actuated position until the release of compression and subsequent disengagement of the securement element 50. For this embodiment, upon actuation, the securement element is deployed by being advanced, whereupon she distal end of the securement element 50 is then urged against either or both of the second guide wire 20 or internal lumen of the second segment. Preferably, the securement element is deployed by being advanced out of the main body segment's distal end and through an opening in communication with the internal lumen of the second segment. Once the distal end of the securement element is inside the second lumen, it is pressed against second guide wire, or preferably wedged between the interior diameter of the second segment and the second guide wire. In this manner, a friction engagement is provided to maintain the second guide wire in the desired position for as long as the securement element remains deployed. As noted above, the distal end of the securement element may incorporate specific features to enhance the holding of the second guide wire in place.

An actuation device capable of causing the releasable securement and release of the second wire may operate by selectively alternating between an engaged and disengaged position. It is recognized that such a device could be created in a number of different ways. For example, the actuating device may operate in a manner similar to a common retractable pen, in the sense that a trigger is actuated to engage and then re-actuated to disengage the securement element. Alternatively, a second trigger mechanism may be provided to cause the disengagement of the securement element.

One embodiment of the actuating device 52 can be seen in an engaged position having the securement element 50 in a deployed position (see FIG. 2A), and having resilient material 56 in a compressed state. Upon the actuator entering into an engaged position, a holding mechanism 54 may be arranged to automatically maintain the engaged position of the holding mechanism until release is appropriate. As shown in the embodiment of FIG. 2B, a second trigger mechanism 55 may be actuated to cause the holding mechanism 54, here shown as a latch, to be released or moved away from a gripping position, whereupon the stored energy in the resilient material 56 is released, and the actuator 52 is returned to a disengaged position, thereby retracting the securement element 50.

Figure 4:
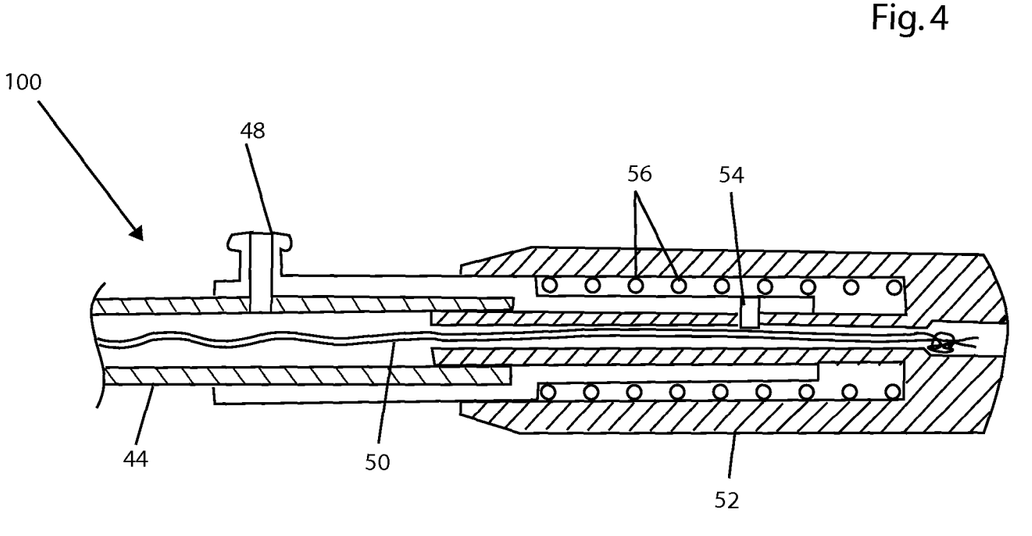
FIG. 4 is a transverse sectional illustration of a possible embodiment of an actuation device having a barrel adapted to engage a filament in tension and maintain that tension by a holding mechanism.

In still another embodiment, as depicted in FIG. 4, the actuation of the securement element 50 may be in response to the engagement of an actuator 52, shown here in the form of a barrel, though it is recognized that other shapes or handles may be suitable and operate in a similar manner. In this embodiment, a barrel may be axially movable relative to the main body 44 of the exchange catheter 100. For example, a barrel may be slidably manipulated, or rotated in order to cause the barrel to advance or retract over a threaded body. As the barrel is axially advanced or retracted, it in turn, acts upon securement element 50 to which it is operationally connected. Optionally, a holding mechanism 54 may be provided to maintain the position of the barrel, and thereby maintain or prevent she deployment of the securement element 50. For example, the holding mechanism 54 may be a fixed slot or protrusion (e.g., a bayonet/groove arrangement) that is arranged to engage and fix the position of the actuator 52, such as where a barrel is rotated to cause the engagement of the holding mechanism. Disengagement of the holding mechanism 54 may be accomplished in a variety of manners, including, further rotation of the barrel, either continuing the rotation, or alternatively, reversing the direction of rotation, whereupon the holding mechanism 54 may disengage and allow the barrel to be returned to its original location and thereby disengage the securement element 50.

It is recognized that the axial movement of the actuator may be accomplished manually in both directions, or alternatively, movement of the actuator in one direction may create a stored energy potential in a resilient material, such as by compressing a compressible material or expanding an elastic material, and upon release, the barrel will return to its original location due to the stored energy driving the return to the original position.

It is also recognized that mechanical actuation of the securement element may also be facilitated by the use of various other methods or devices, including but not limited to, electromechanical, or magnetic actuation, e.g., solenoid. Alternatively, actuation of the securement element may be entirely manual as has been previously described, but rely on alternative mechanical elements (e.g., gear, lever or screw actuation) to drive the securement element against the other components of the system, which may offer quicker response or increased leverage to effect the securement. It is also recognized that rather than a simple friction fit, the securement element may feature a keyed arrangement, or male/female arrangement, where the securement element is arranged to fit into or against another receiving element (e.g., a port, a recess, a protrusion, etc.) that will allow the second guide wire to become immobilized.

There may be a benefit, in some embodiments, to provide a component that minimizes trauma to the vessel walls as the system is being pushed through the anatomy, for example, as might occur if the distal opening would catch on tissue as the exchange catheter is advanced through the body. This trauma may be minimized, for example, by including a lip, flexible door, or valve, for at least one of the exposed openings on the exchange catheter, in order to minimize the profile of the catheter tip and prevent the occurrence of tissue trauma. In these embodiments, the trauma-minimizing component may cover or shelter an otherwise exposed edge of the opening as the catheter is advanced. In embodiments where the added component obscures at least partially on the opening being sheltered, the shielding component may be provided in such a fashion that it can be deflected as a wire is advanced out from the opening. Various methods known in the art (e.g., flaps, stretchable sleeves, duck-bill valves, trap doors, etc.) can be used. Alternatively, the exposed edge of the opening may be shaped, e.g., rounded or curved, in order to minimize the likelihood of catching on tissue.

Figure 5:
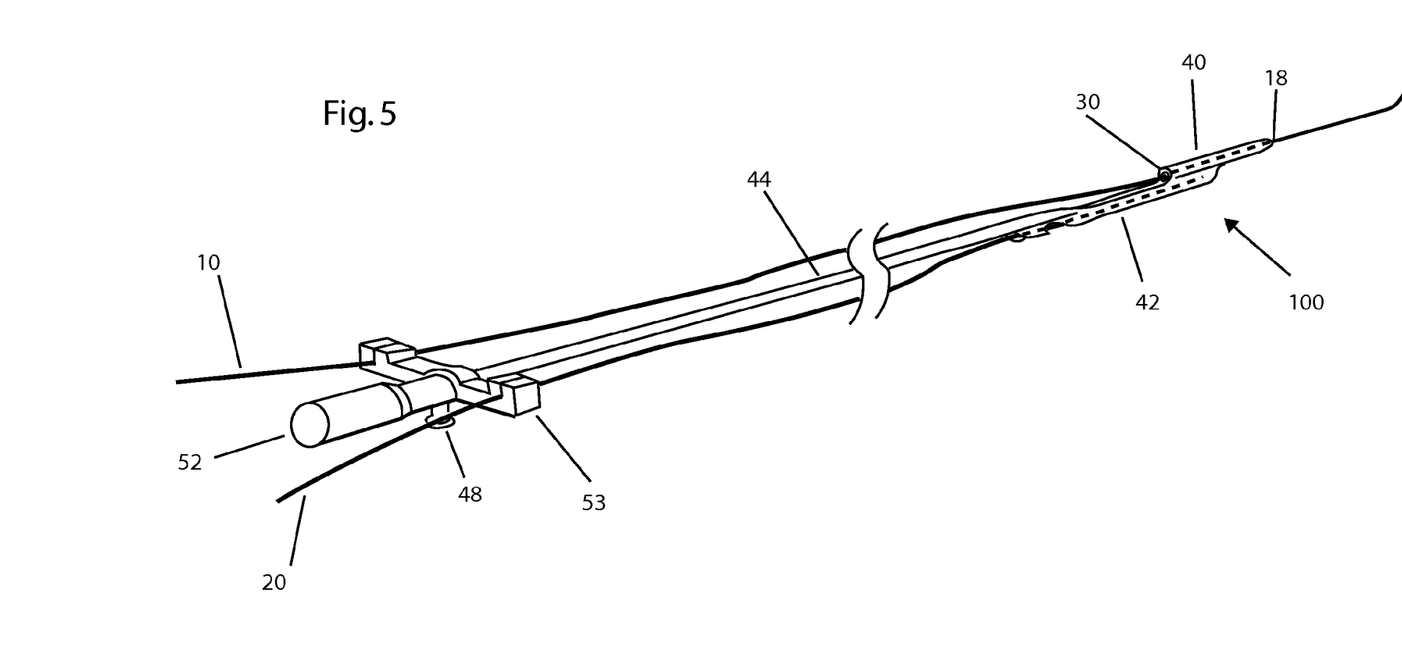
FIG. 5 is an illustration of an embodiment of the guide wire exchange catheter shown in FIG. 1, further featuring at the proximal portion the barrel actuation mechanism of FIG. 4, a port for the introduction of materials, and a manifold to releasably grip and control the portion of the first and second wires that remains outside of the body.

In the practice of the present invention, the introduction of multiple guide wires into the body, along side and/or in a catheter, may make manipulating a particular system component difficult. In order to prevent confusion or entanglement of the various components, and to provide an orderly cascade of system components, there may be a benefit to providing a manifold device 53 at or near the proximal end of the exchange catheter 100, as can be seen in FIG. 5. Such a manifold device may be permanently attached to the exchange catheter 100, or alternatively, may be releasably secured. The manifold 53 may be utilized to selectively secure at least a portion of multiple system components, especially guide wires that are extending outside of the body during the procedure. Such a manifold 53 could consist of a support frame, into which, some or all of the components are fitted, and retained in their location within the support frame, either by friction engagement in a slit or an opening arranged to house the inserted component, or alternatively, at least one clamping device or clip (not shown) may be provided to maintain the secure engagement of the manifold and the system components to be retained in position. The support frame may also feature materials, inserts or shapes that assist in retaining the components in their respective locations, for example, a frame supporting an elastic material would allow the guide wire to be inserted into a slit cut into the block of elastic material, where the elastic properties of the material cause it to grip the wire and maintain it in a desired location as it is elastically deformed around the inserted component. It is also recognized that such a manifold device 53 could be used in conjunction with marking, coloring, or otherwise identifying the components, e.g., labels, colored bands or coatings applied to the components, especially guide wires, in order to assist in component identification, thereby serving to minimize confusion and the risk of entanglement and assist the operator in selecting the appropriate system component at the correct step of the procedure.

In the practice of the various embodiments of the invention described herein, there may be a benefit to priming a tubular lumen formed in the exchange catheter with a liquid material, in order to remove the potential for introducing or releasing a gas bubble into the patient. For example, the main body segment 44 of FIG. 1 features a tubular main body 44, through which is directed the securement element 50, shown here as a looped filament. It may be necessary to ensure that the balance of the lumen of the main body segment is filled with fluid, as may be accomplished simply by directing fluid into the lumen of the main body segment. Alternatively, as depicted in FIG. 4, a port 48 may be provided, for example in a manifold 53 at the proximal end of the system, through which fluid may be introduced to prime or displace any gas in the system. The system may also beneficially incorporate other features to prevent the introduction of gas bubbles, including but not limited to the introduction of sealants, valves, or o-rings that would either serve to prevent the escape of gas while inserted into the patient, or more likely prevent the escape of fluid from within the primed lumen, before and during the introduction of the system into the patient. Additionally, the port 48 may be useful for the introduction of materials into the body, where liquids, gasses, or solids may be introduced through port 48, and directed through lumen 38 of the main body segment, as has been discussed previously. It is recognized that the securement element 50 may be removable from the system, such that after delivery of the second guide wire, the securement element may be removed to leave the lumen 38 clear for the introduction of materials therethrough.

One embodiment of the present invention provides for a simple, easy to use device suitable for facilitating the exchange of guide wires in a living being in a safe, efficient and secure manner. For a procedure requiring the exchange of one guide wire with a second guide wire, the present invention obviates the need for double-length guide wires, as required for prior art OTW and RE catheters, where the double length of the guide wire tends to be difficult to work with due to the excess length remaining outside of the body in order to allow the removal the exchange catheter. Additionally, the present invention overcomes a difficulty of MX catheters, where exchange of a guide wire is performed by unzipping or laterally removing the guide wire through a lengthy slit in the exchange catheter; as such removal or unzipping may be time consuming and frequently results in unwanted shifting of the guide wire placed inside the body or of damage to the wire as it is being disengaged through the lengthy slit.

The present invention, with reference to the exemplary embodiment of FIG. 1, provides for a securement or locking mechanism, including securement element 50, used in conjunction with the exchange catheter 100, as has previously been described, that allows the releasable securement of the secondary guide wire 20 to the exchange or shuttle catheter 100. After the secondary guide wire is releasably secured to the exchange catheter 100 by the actuation of securement element 50, the secondary guide wire and exchange catheter may together be maneuvered (e.g., advanced into, or retracted from the patient) with the exchange catheter serving to pull along the securely attached second wire's proximal end, and by virtue of the securement mechanism, the exchange catheter and second wire are prevented from separating or diverging during the maneuvering. The advancement of the exchange catheter will typically be along a primary guide wire, which having been previously inserted, allows the exchange catheter to follow along its path in a monorail fashion. After arriving at or near a desired site, preferably distal to a lesion, the securement element 50 may then be disabled or disengaged, thereby allowing each of the secondary guide wire 20 and the exchange catheter 100 to be moved independently of the other.

It is recognized that in other embodiments of the practice of the present invention, the second guide wire 20 may be alternately released and secured, and may be employed to traverse tortuous vessels or other difficult crossings by repeatably releasing, slidably manipulating, and securing the guide wire from the exchange catheter 100 when deemed appropriate by the operator. For example, the exchange catheter 100 may be advanced through the body, following along the path set by a previously inserted guide wire 10, and carrying along the second guide wire 20. In order to advance more distally into the patient, the second guide wire 20 may be released, and advanced, while leaving the exchange catheter in a fixed position. After traversing or encountering a difficult region with the second guide wire, for example a constricted or tortuous region, there may be benefit to advancing the exchange catheter along the path established by the second guide wire. Alternatively, the operator may selectively secure the second guide wire 20 to the catheter 100 using the securement mechanism 50, such that the distal end of the exchange catheter 100 is now secured to an intermediate portion of the second guide wire 20, away from the proximal and distal ends. As the exchange catheter 100 may provide better pushability relative to the soft, more flexible guide wire, the exchange catheter may then be advanced, and by virtue of being secured to the second guide wire 20, such advancement of the catheter 100 will advance the second guide wire 20 as well. Additionally, as the secure connection of the second guide wire 20 to the distal end of the exchange catheter 100 is at a point inside the body, it is recognized that advancing the exchange catheter 100 from outside the patient, will in turn serve to advance the second guide wire 20, where the pushing action is now occurring at the location where the guide wire is secured to the exchange catheter. In this manner, the distance the pushing force is transmitted through the guide wire may be significantly less than the total distance the guide wire is inserted into the body, thereby reducing the tendency of the guide wire to buckle or distort.

It is also recognized that providing a secondary guide wire 20 alongside the first guide wire 10, and by maintaining the two guide wires in position alongside of each other by the exchange or shuttle catheter 100, the flexibility or stiffness of the distal end of either the first or second guide wire may be manipulated. For example, by slidably moving one guide wire relative to the other, the stiffness at the distal end of the further extending guide wire may be adjusted, increasing stiffness by bringing each of the distal ends in closer proximity, or decreasing stiffness of the further extended guide wire by increasing the spacing between the two distal ends. Furthermore, it is recognized that the securement element in the form of a wire or rod may also be of benefit in increasing the stiffness of the exchange catheter, or alternatively, a flexible filament of another embodiment of a securement element may minimize the stiffness. The operator may select one over the other in order to meet a required stiffness or flexibility requirement for a particular procedure.

In another embodiment, where the first and second guide wires are in position alongside of each other, there may be a benefit to providing a securement mechanism, including a securement element as has been described previously, that is arranged to secure the primary guide wire while in position within the first segment. By providing a means to secure the primary guide wire within the first segment, preferably in addition to securing a secondary guide wire within a second segment, an operator may be able to selectively secure one guide wire in place, and slidably manipulate the other one, in this manner, the operator may selectively utilize a guide wire having one set of properties or characteristics, until it becomes more beneficial to change guide wires and take advantage of the other guide wire's properties or characteristics. For example, where a primary guide wire is relatively stiff, and a secondary guide wire is more flexible or provides shape memory, it is possible to advance the first guide wire into the body until there is a need for a more flexible guide wire. Thereupon the exchange catheter, with a second, more flexible guide wire secured in the second lumen, may be advanced, where the exchange catheter follows the path of the first guide wire due to the first guide wire being directed through the first segment of the exchange catheter, in a monorail fashion. Upon the exchange catheter arriving at or near the distal end of the first wire, the first wire may be secured within the first segment by actuating the securement mechanism for the first segment. Subsequently, the second wire may be released by disengaging the securement mechanism for the second segment, and the second wire may then be advanced out from the distal end of the second segment. After advancing the second wire to a desired location, the operator may hold the second wire in position, and advance the exchange catheter, now following along the second guide wire path with the second segment serving as a monorail lumen, and carrying along the first wire, which is secured in the first segment.

The procedures described herein are directed to guide wire exchange procedures which can be performed, for example, in the patient's vasculature utilizing various embodiments of the present invention, it should be appreciated by those skilled in the art that any one of a number of interventional procedures in within the body could utilize the subject invention for treatment as web. Moreover, the present invention can be utilized in a number of other body vessels and tissues including, but not limited to, the arteries, veins, grafts, urinary tracts, bladders, intestines, fallopian tubes and other body tissues, cavities and orifices.

In one exemplary procedure for using the present invention, a wire is introduced into the patient's vasculature in a conventional Seldinger technique, or any suitable variation of that procedure for inserting a wire into a vessel or tissue of a living being. The practice of the Seldinger technique generally involves identifying the target vessel, puncturing the vessel, and inserting a guide wire. A vessel dilator may then be inserted over the guide wire and pushed through the vessel wall to create a larger opening. The dilator may then be removed, leaving the guide wire remaining in place and a guide catheter or catheter sheath may be inserted over the guide wire and pushed into the vessel. The primary guide wire 10 is then placed within the patient's vasculature and may be maneuvered through the vasculature to arrive at a desired location, which may be at or near the area to be treated, preferably the desired location is past the area of treatment at a downstream location. After the primary guide wire is in place, the exchange or shuttle catheter 100 of the various embodiments of the present invention (for example, see FIG. 1) is prepared for insertion by securing the distal end of the second wire 20 in place within the second segment or shuttle lumen 42, by actuating or deploying the securement element 50. The combined catheter and second wire can then be back loaded onto the proximal end of the first guide wire 10, by directing the proximal end of the primary wire 10 into the distal opening 18 of the exchange catheter, and out of the proximal opening of the first segment. It is recognized that the insertion into, and securement of the second wire to, the exchange catheter's second segment may also be performed after the primary wire is backloaded through the first segment. Once the primary wire is directed entirely through the first segment, the physician can then advance the exchange catheter 100 over the primary guide wire 10 using techniques known in the art. As the first guide wire is directed through the first segment of the exchange catheter, the first segment will serve as a guide wire following lumen, ensuring that the distal end of the exchange catheter will navigate down the path of the first guide wire as the exchange catheter is advanced. Furthermore, as the distal end of the second guide wire is securely fixed inside the second lumen of the exchange catheter, the second wire will then be pulled along by the advancement of the exchange catheter, such that the second wire will, also follow the path of the first guide wire as well. By the use of the various embodiments of the device, where a wire's distal end may be secured to a catheter and pulled along by the advancement of the catheter, it becomes possible to introduce system components (e.g., wires, threads, string, filaments, etc.) that are incapable of being advanced into the body by being pushed, as the components would not be compatible with an advancement requiring pushing from outside the body, for example where the component might be likely to buckle, fold, collapse, or otherwise fail during advancement. With the system and devices described herein, when combined with these components that are incompatible with being advanced by pushing, it become possible to deliver such a component, by providing for it to be pulled to the target site. Such an embodiment may be useful, for example, where it becomes necessary to deliver a thin wire, such as a flexible pacer lead, or other thin flexible filament, into a body, where the filament is incapable of being delivered by being pushed into the body. For the practice of this embodiment, the pacer lead may feature a distal end that provides for attachment, such as anchors or barbs at or near the distal end, where barbs catch a target site, such as tissue or implant, and becomes lodged in place, with the filament then extending proximally from the site.

Once the exchange catheter 100 and second wire 20 are in the desired location within the body, the securement element 50 may be disengaged, thereby allowing independent movement of the second guide wire 20 relative to the exchange catheter 100. Optionally, the primary guide wire 10 may be removed entirely from the body or withdrawn at least partially, especially in those embodiments of the exchange catheter where the first and second segments merge or share the distal opening 18 of the exchange catheter, where removal of the primary wire may be necessary to enable the advancement of the second wire through the distal opening 18 or an extended segment 36, as has been described previously (See FIGS. 2A, 2B, and FIG. 3). After the operator is satisfied with the positioning of the second guide wire, the exchange catheter may also be retracted at least partially or removed entirely from the patient, while leaving the second guide wire in place. In this manner, the operator may use the second wire 20 for guiding additional catheters into the patient, using techniques known in the art.

Alternatively, after the second guide wire 20 is in place at the desired location, and after the securement element 50 has been disengaged, the second guide wire may be independently advanced distally into the patient, while maintaining the exchange catheter 100 in a desired position within the body. Once the second guide wire has been directed further into the body (in a distal direction) using techniques known in the art to arrive at a second location, it is recognized that the exchange catheter may then be advanced along the path of the second guide wire, which may be maintained in a fixed axial position, at a desired location within the body. The exchange catheter may be advanced along the length of the second guide wire at least until the exchange catheter approaches the distal end of the second guide wire, whereupon the securement element may be engaged. Preferably, the exchange catheter would not be advanced along the path of the second wire to the extent that the second guide wire's distal end would exit or be directed proximally through the proximal opening of the second segment. In this way, the second guide wire and exchange catheter may again be secured together and advanced further into the patient. It is recognized that the exchange catheter may be utilized to augment or provide increased pushability or enhanced characteristics useful for the advancement and control of the guide wire that may be needed in order to be advanced or directed through particular regions of the vasculature, such as crossing a difficult lesion.

It is recognized that the various embodiments of the present invention may be altered to incorporate repetition of the described features in order to facilitate the exchange of more than one guide wire. That is, by incorporating additional lumen-forming segments or monorails near the distal region of the exchange catheter, as well as additional securement elements for each additional guide wire, and optionally actuating devices, it becomes possible, in a manner similar to as has been described previously, for an exchange catheter to have secured more than one guide wire near its distal end, where multiple exchanges of a guide wire are possible by repeatably practicing the guide wire exchange procedure as has already been described.

Although the foregoing invention has, for purposes of clarity and understanding, been described in some detail by way of illustration and example, it will be obvious to familiar with the art that certain changes and modifications may be practiced which will still fall within the scope of the appended claims. It will also be understood that each feature of each embodiment discussed herein, and of each reference cited herein, can be used in combination with the features of any other embodiment.

What is claimed is:

1. A catheter system for positioning a second guide wire adjacent to a first guide wire, said first guide wire located within a lumen in a living being, said catheter system comprising:
    an exchange catheter having at least first and second lumen segments and a reversible securement mechanism arranged to be engaged and disengaged, and while in an engaged position said reversible securement mechanism releasably and reversibly holds said second guide wire in a fixed position at or near a distal end of said exchange catheter, and wherein said first lumen segment is slidably arranged over said first guide wire to guide said catheter system along said first guide wire, and further wherein each of said first and second lumen segments comprises a distal opening, and said distal opening of said first lumen segment is distinct from said distal opening of said second lumen segment.

2. The catheter system of claim 1, wherein said guiding occurs prior to said securement mechanism being placed in a disengaged position.

3. The catheter system of claim 1, wherein said guiding occurs following said securement mechanism being re-placed in an engaged position.

4. The catheter system of claim 1, wherein said second lumen segment is positioned over a distal end of said second guide wire and said distal end of said second guide wire is maintained by said securement mechanism in a secure position in said second lumen segment.

5. The catheter system of claim 4, further comprising a shielding component protecting the distal opening of said second lumen segment, with said shielding component being movable between a first position and a second position, said first position of said shielding component at least partially closing the distal opening of the second lumen segment containing said second guide wire, and said second position of said shielding component permitting the slidable movement of said second guide wire relative to said exchange catheter.

6. The catheter system of claim 1, further comprising the first and second guide wires.

7. The catheter system of claim 6, wherein at least a portion of said first and second guide wires are marked.

8. The catheter system of claim 6, wherein neither said first or second wires is a double-length wire.

9. The guide wire exchange system Of claim 6, wherein said second guide wire is different from said first guide wire in at least one material property.

10. The guide wire exchange system of claim 9, wherein said material property is selected from the group consisting of: stiffness, flexibility, distal end shape, construction, material, diameter, and shape memory.

11. The catheter system of claim 6, wherein said second wire is an electrophysiology wire.

12. The catheter system of claim 6, wherein said second wire is not capable of effectively being advanced into a being by pushing from the proximal end.

13. The system of claim 1, where the securement mechanism comprises a securement element selected from the group comprising a wire loop, a filament loop, a multi-stranded loop, a wedge, a wire, or rod.

14. The catheter system of claim 13, wherein said securement mechanism further comprises a reversible actuator mechanism for engaging said securement element and holding said second guide wire in a fixed position relative to a portion of said exchange catheter.

15. The catheter system of claim 1, wherein there is longitudinal overlap between said first and second lumen segments.

16. The catheter system of claim 1, wherein said exchange catheter further comprises a main body segment of tubular construction that tapers from a larger to a smaller outside diameter from a proximal end to a distal end.

17. A guide wire exchange system comprising at least two guide wires and an exchange catheter comprising a tubular main body segment having a lumen running therethrough, and a first and second segment located near the distal end of the exchange catheter, each of the segments forming a lumen for the passage of a guide wire therethrough, wherein said first guide wire is directed through said first segment, and said second guide wire is directed into said second segment, said exchange catheter further comprising at least one reversible securement mechanism comprising a securement element located at or near said distal end of said exchange catheter, said securement element arranged to reversibly and releasably secure said second guide wire in said second segment.

18. The guide wire exchange system of claim 17, wherein said reversible securement mechanism is arranged such that said second guide wire and said second segment are manipulated in a synchronous manner while secured by said securement element.

19. The guide wire system of claim 18, wherein said reversible securement mechanism further comprises an actuator provided near the proximal end of the exchange catheter arranged to releasably engage and disengage said securement element with said second guide wire.

20. The guide wire system of claim 19, wherein said actuator is further arranged to repeatedly engage and disengage said securement element with said second guidewire.

21. The guide wire system of claim 19, wherein said actuator mechanism comprises a locking mechanism with at least a portion of which is arranged to be compressed while maintaining said securement element in an engaged condition, such that upon release of said locking mechanism, said compressed portion moves said securement element away from said engaged condition to a disengaged position.

22. The guide wire catheter of claim 18, wherein said securement element is one of a flexible filament loop arranged to secure when placed in tension, or a wire arranged to secure when placed in compression.

23. The guide wire exchange system of claim 22, where the securement element is arranged to secure when placed in compression, the securement element further comprises a wedge-shaped distal end.

24. The guide wire exchange system of claim 22, where the securement element is arranged to secure when placed in compression, the securement element further comprising an enlarged distal end.

25. The guide wire exchange system of claim 18, wherein said second guide wire is secured at an intermediate portion of said second guide wire, such that a force applied at the proximal end of said exchange catheter causes the advancement of said exchange catheter, and further advance said second guide wire from said secured intermediate portion, thereby minimizing a distance said second guide wire transmits said advancing force.

26. The guide wire exchange system of claim 17, wherein said main body segment, said first and second segments are parallel, and wherein said second segment is laterally adjacent an axis of the main body segment.

27. The guide wire exchange system of claim 17, wherein said main body segment, said first and second segments form a continuous tubular form having an internal lumen extended therethrough, with lateral openings provided at the proximal end of each of the first and second segments.

28. The guide wire exchange system of claim 17, wherein said main body segment varies in flexibility along its length, having increased stiffness at its proximal end and decreased stiffness at its distal end.

29. The guide wire exchange system of claim 17, wherein said exchange catheter further comprises at least one radio-opaque marker.

30. The guide wire exchange system of claim 17, wherein a distal end of said second segment merges with said first segment forming a merger point, and said exchange catheter extends distally from the merger point as an extended distal section arranged to accept said first and second guide wires.

31. The guide wire exchange system of claim 30, wherein said extended distal section provides an extended low profile and is sized to accommodate only one of said first guide wire and said second guide wire at one time.

32. The guide wire exchange system of claim 17, wherein said lumen of said main body segment is arranged to accept said securement element with minimal clearance.

33. The guide wire exchange system of claim 17, wherein said lumen of said main body segment is arranged to accept said securement element with clearance provided for the delivery of additional material through said lumen of said main body segment.

34. The guide wire exchange system of claim 33, wherein said additional material is selected from the group consisting of blood, saline, contrast fluid, therapeutic agents, biologically active agents, particulates, microspheres, drugs and combinations thereof.

35. The guide wire exchange system of claim 33, wherein said main body segment further comprises a port.

36. The guide wire exchange system of claim 17, wherein said second segment comprises a shielding component at least partly covering a distal opening of said second segment.

37. The guide wire exchange system of claim 17, wherein said exchange catheter further comprises a manifold device near the proximal end of the exchange catheter.

38. The guide wire exchange system of claim 17, wherein said second guide wire is different from said first guide wire in at least one characteristic selected from the group consisting of: stiffness, flexibility, distal end shape, construction, material, diameter, and shape memory.

39. A catheter system for positioning a second guide wire adjacent to a first guide wire, said first guide wire located within a lumen in a living being, said catheter system comprising:

> an exchange catheter having at least first and second lumen segments positioned toward a distal end of said exchange catheter, and a reversible securement mechanism arranged to be reversibly engaged and disengaged, and while in an engaged position said securement mechanism releasably holds said second guide wire in a fixed position relative to a portion of said exchange catheter, said releasably holding occurring at or near said distal end of said exchange catheter, and wherein said first lumen segment is slidably arranged over said first guide wire to guide said catheter system along said first guide wire, and further wherein said first and second lumen segments are parallel to one another and do not share a common axis.

\* \* \* \* \*